(12) United States Patent
Chen et al.

(10) Patent No.: US 11,819,614 B2
(45) Date of Patent: Nov. 21, 2023

(54) PATIENT INTERFACE HAVING ADAPTIVE SYSTEM, RESPIRATORY MASK AND CUSHION MODULE ADAPTED WITH ADAPTIVE SYSTEM

(71) Applicant: APEX MEDICAL CORP., New Taipei (TW)

(72) Inventors: Chun-hung Chen, New Taipei (TW); Chih-tsan Chien, New Taipei (TW); Pi-kai Lee, New Taipei (TW); Yu-chen Liu, New Taipei (TW); Chia-wei Huang, New Taipei (TW); Shin-Lan Lin, New Taipei (TW)

(73) Assignee: APEX MEDICAL CORP, New Taipei (TW)

( * ) Notice: Subject to any disclaimer, the term of this patent is extended or adjusted under 35 U.S.C. 154(b) by 910 days.

(21) Appl. No.: 16/452,974

(22) Filed: Jun. 26, 2019

(65) Prior Publication Data
US 2020/0001034 A1 Jan. 2, 2020

(30) Foreign Application Priority Data
Jul. 2, 2018 (TW) .................................. 107122854

(51) Int. Cl.
*A61M 16/06* (2006.01)
*A61M 16/08* (2006.01)

(52) U.S. Cl.
CPC .... *A61M 16/0644* (2014.02); *A61M 16/0622* (2014.02); *A61M 16/0683* (2013.01); *A61M 16/0816* (2013.01)

(58) Field of Classification Search
CPC .............. A61M 16/06; A61M 16/0611; A61M 16/0616; A61M 16/0622; A61M 16/0633; A61M 16/0638; A61M 16/0644; A61M 16/0683; A61M 16/08; A61M 16/0816; A61M 16/0825; A61M 16/0875; A61M 2205/42; A61M 2205/581;
(Continued)

(56) References Cited

U.S. PATENT DOCUMENTS 5,243,971 A * 9/1993 Sullivan ................ A61M 16/06
128/207.18
5,662,101 A * 9/1997 Ogden .............. A61M 16/0683
128/912

(Continued)

*Primary Examiner* — Annette Dixon
(74) *Attorney, Agent, or Firm* — WPAT, P.C.

(57) ABSTRACT

The present invention discloses a patient interface having an adaptive system, a respiratory mask and a cushion module adapted with the adaptive system. The adaptive system includes a forehead pressure diffusing portion, a cheek buffering portion and a connecting portion. The forehead pressure diffusing portion is disposed in a frame module. The cheek buffering portion is disposed in a cushion module. The connecting portion is positioned between the forehead pressure diffusing portion and the cheek buffering portion. The connecting portion is configured to transmit pressure between the forehead pressure diffusing portion and the cheek buffering portion. Thus, when a user wears a mask or other devices with the adaptive system, a force received by the face of the user could be automatically and appropriately distributed, further improving comfort of the wearer.

29 Claims, 11 Drawing Sheets

(58) Field of Classification Search
CPC .......... A61M 2210/0618; A62B 18/084; Y10S 128/912; Y10T 29/49826
See application file for complete search history.

(56) References Cited

U.S. PATENT DOCUMENTS

| | | | | |
|---|---|---|---|---|
| 6,112,746 | A * | 9/2000 | Kwok | A61M 16/0683 128/206.26 |
| 10,173,024 | B2 * | 1/2019 | Kooij | A61M 16/06 |
| 2007/0044804 | A1 * | 3/2007 | Matula | A61M 16/06 128/206.21 |
| 2008/0314388 | A1 * | 12/2008 | Brambilla | A61M 16/0622 128/205.25 |
| 2010/0294281 | A1 * | 11/2010 | Ho | A61M 16/0633 128/206.24 |
| 2012/0138061 | A1 * | 6/2012 | Dravitzki | A61M 16/0875 128/205.25 |
| 2013/0008448 | A1 * | 1/2013 | Todd | A61M 16/0633 128/205.25 |
| 2014/0305438 | A1 * | 10/2014 | Neff | A61M 16/06 29/428 |
| 2018/0071475 | A1 | 3/2018 | Howard et al. | |

* cited by examiner

PATIENT INTERFACE HAVING ADAPTIVE SYSTEM, RESPIRATORY MASK AND CUSHION MODULE ADAPTED WITH ADAPTIVE SYSTEM

BACKGROUND OF THE INVENTION

Field of the Invention

The present invention relates to an adaptive system suitable for a breathing device and, more particularly, to a patient interface having an adaptive system, a respiratory mask and a cushion module adapted with the adaptive system.

Description of the Prior Art

A continuous positive pressure respirator is a type of equipment for treating obstructive sleep apnea (OSA). By using a patent interface covering the nose of a user or simultaneously covering the mouth and nose of a patient, air or other breathable gases is supplied to a patient using the respirator, and a continuous positive pressure is maintained to open up an obstructed respiratory tract of the patient and to keep the respiratory tract clear, thereby achieving the object of treating OSA.

For either a continuous positive pressure respiratory device or other supply devices for supplying breathable gases to a user, a supply environment needs to be set up on the face of a wearer. This supply environment needs to provide appropriate airtightness, so as to allow the respiratory device or the supply device to successfully supply air or other breathable gases to the user by means of the pressurization and the appropriate airtightness provided by the supply environment.

The supply environment is usually provided by a mask covering the mouth and nose of the user, and a binding strap is used to fix the mask on the face of the user to allow the supply environment to provide the appropriate airtightness. However, under extended period of wearing of the user, in order to allow the supply environment to provide the appropriate airtightness, the user may often feel uncomfortable from the tight binding forces on the face and head of the user over an extended period of application.

SUMMARY OF THE INVENTION

It is an object of the present invention to provide comfort to a user using a continuous positive pressure respiratory device or other supply devices supplying breathable gases to the user.

To achieve the above and other objects, a patent interface is provided according to an embodiment of the present invention. The patient interface includes a cushion module, an elbow module, a frame module, a headgear, and a patient interface having an adaptive system. The frame module is positioned between the cushion module and the elbow module, and the headgear is removably attached to the frame module. When the cushion module, the elbow module, and the headgear are assembled, the adaptive system is adapted to fit the contours of patient's face. The adaptive system includes a forehead pressure diffusing system, a cheek buffering portion and a connecting portion. The forehead pressure diffusing portion is disposed in the frame module. The cheek buffering portion is disposed in the cushion module. The connecting portion is positioned between the forehead pressure diffusing portion and the cheek buffering portion, wherein the connecting portion is configured to transmit pressure between the forehead pressure diffusing portion and the cheek buffering portion.

In one embodiment, the forehead pressure diffusing portion comprises a headgear connecting portion, and two side wings deformable by a pressure applied on the headgear.

In one embodiment, a forehead pad is absent between the forehead pressure diffusing portion and the forehead of the wearer.

In one embodiment, the headgear connecting portion has a through hole for the headgear to pass through.

In one embodiment, the headgear connected to the headgear connecting portion serves as a contact interface between the frame module and the forehead of the wearer.

In one embodiment, each of the side wings comprises an indentation for providing deformation.

In one embodiment, a width of the indentation on each of the side wings is at least 1 mm.

In one embodiment, each of the side wings is configured to laterally extend at an end portion of the frame module, and a side edge of each of the side wings is distanced from a center line of the corresponding indentation by at least 4 mm.

In one embodiment, the side wings are made of a material different from that of the headgear connecting portion, and an elasticity of the side wings is greater than that of the headgear connecting portion.

In one embodiment, the frame module includes a body, the connecting portion and two lateral extension elements. The body is for assembling the elbow module and the cushion module. The connecting portion extends from the body, and has an end portion thereof as the forehead pressure diffusing portion. The two lateral extension elements extend respectively from two sides of the body, and an end portion of each of the two lateral extension elements is provided with a through hole for the headgear to pass through.

To achieve the above and other objects, a cushion module adapted with an adaptive system and used for assembling to a frame module is provided according to an embodiment of the present invention. The cushion module includes a deformation portion and a non-deformation portion. The deformation portion includes a first coupling region, a nose region, a buffer region and a face contacting region. The buffer region extends downwards from the nose region. The non-deformation portion includes an assembly region and a second coupling region. The assembly region is for detachably assembling to the frame module, and the second coupling region is permanently coupled to the first coupling region.

In one embodiment, in the deformation portion, an elasticity of the buffer region is greater than those of the first coupling region, the nose region and the face contacting region.

In one embodiment, the deformation portion and the non-deformation portion are shaped and coupled by wrapped injection.

In one embodiment, the non-deformation portion comprises at least one release opening region, the release opening region is configured near the nose region of the deformation region and has a plurality of vent holes, and the vent holes are distributed near above two nose wings of a wearer when the frame module is worn.

In one embodiment, the buffer region comprises a longitudinally extended groove on each of inner side edges of the deformation portion.

In one embodiment, a width of each of the grooves appears tapered from top to bottom or conic.

In one embodiment, in the deformation portion, a cushion thickness of the grooves of the buffer region is smaller than cushion thicknesses of the nose region and the face contacting region.

In one embodiment, a cushion thickness of the grooves of the buffer region is smaller than a longitudinal extended depth of the grooves.

In one embodiment, in the non-deformation portion, the assembly region comprises at least one assembly structure.

In one embodiment, the face contacting region of the deformation portion comprises a wearing port covering only the nose of a wearer or simultaneously covering the mouth and nose of the wearer.

In one embodiment, the buffer region serves as a buffer interface for the pressure applied between the frame module and the face of a wearer by using an appropriate configuration of a cushion material or thickness of the buffer region, such that the deformation portion is adaptively fitted to the face of the wearer when the frame module is worn.

To achieve the above and other objects, a respiratory mask is provided according to an embodiment of the present invention. The respiratory mask includes a cushion module, an elbow module having an air duct, a frame module configured between the cushion module and the elbow module, a headgear removably attached to the frame module, a connecting ring, a covering ring and an adaptive system. The connecting ring is configured at a coupling opening on a body of the frame module for the elbow module and the cushion module to be detachably assembled to the frame module through the connecting ring. The covering ring covers the connecting ring and reveals the air duct, and includes an inclined surface on a surface opposite to the frame module. When cushion module, the elbow module, and the headgear are assembled, the adaptive system is adapted to fit the contours of patient's face.

In one embodiment, the connecting ring includes an inner pipe portion, and an outer periphery portion connected to the inner pipe portion and encircling the inner pipe portion. The elbow module is detachably assembled to the inner pipe portion, the outer periphery portion and a flange on the body of the frame module form an assembly gap for receiving a front air transporting opening of the cushion module, and the cushion module is detachably assembled to the body of the frame module through the assembly gap.

In one embodiment, a periphery of the front air transporting opening of the cushion module is provided with an assembly collar, an inner diameter of the assembly collar gradually shrinks backwards, and the flange on the body of the frame module is matchingly used to form abutment between an inner surface of the assembly collar of the cushion module and an outer surface of the outer periphery portion of the connecting ring to enhance airtightness.

In one embodiment, the inner pipe portion of the connecting ring comprises a fastening edge at an end portion protruding from a front surface of the frame module, the front surface of the body is provided with an extension flange encircling the coupling opening, the fastening edge is for fastening to the extension flange, the outer periphery portion of the connecting ring is provided with a step structure, and the step structure is for abutting near the flange of the body.

In one embodiment, an inner side of the extension flange of the body comprises a positioning rod, and the outer periphery portion of the connecting ring has a positioning hole for the positioning rod to pass through.

In one embodiment, the covering ring comprises an inclined portion and a planar portion, the inclined portion has the inclined surface and encircles an outer side of the planar portion, and an included angle between the inclined surface and a horizontal reference plane of the planar portion is between 0 degree and 90 degrees.

In one embodiment, an outer edge of the covering ring and the cushion module are distanced by a flow guide gap of 0.1 mm to 5 mm.

In one embodiment, the inclined surface of the covering ring enables water in the respiratory mask to flow downwards along the inclined surface of the covering ring and an inner arc surface of the cushion module, and to gather at a folded portion on an inner side of the cushion module.

In one embodiment, a material of the covering ring is a hydrophobic material.

In the embodiments of the present invention, with the configuration of the adaptive system, a force received by the face of a user could be automatically and appropriately distributed when the user wears a mask or other devices forming a supply environment, thus improving comfort of a wearer.

DETAILED DESCRIPTION OF THE EMBODIMENTS

In the disclosure, descriptive terms such as "include, comprise, have" or other similar terms are not for merely limiting the essential elements listed in the disclosure, but can include other elements that are not explicitly listed and are however usually inherent in the components, structures, devices, systems, portions or regions.

In the disclosure, the terms similar to ordinals such as "first" or "second" described are for distinguishing or referring to associated identical or similar components or structures, and do not necessarily imply the orders of these components, structures, portions or regions in a spatial aspect. It should be understood that, in some situations or configurations, the ordinal terms could be interchangeably used without affecting the implementation of the present invention.

In the disclosure, descriptive terms such as "a" or "one" are used to describe the component, structure, device, system, portion or region, and are for illustration purposes and providing generic meaning to the scope of the present invention. Therefore, unless otherwise explicitly specified, such description should be understood as including one or at least one, and a singular number also includes a plural number.

Figure 1:
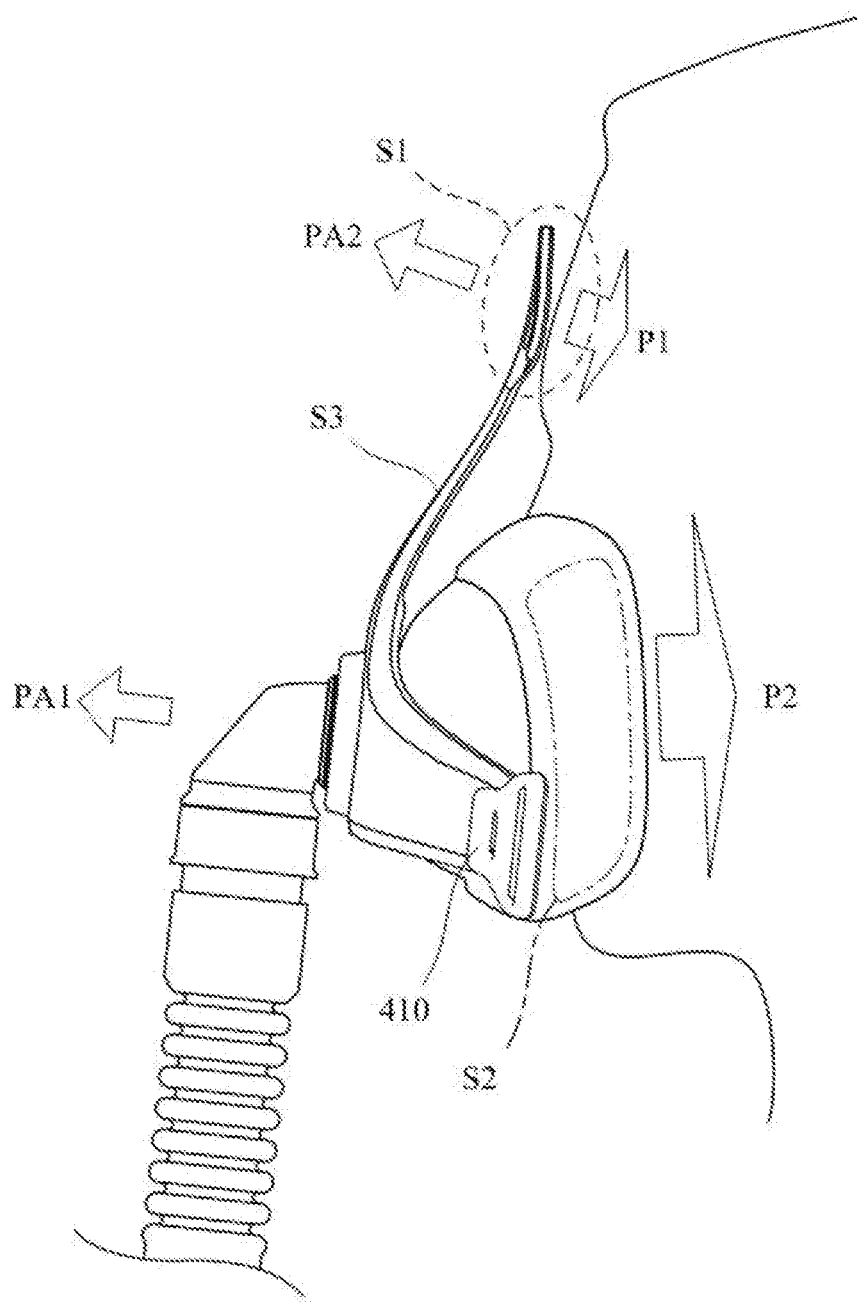
FIG. 1. is a schematic diagram of an adaptive system of the present invention.

Refer to FIG. 1 showing a schematic diagram of an adaptive system of the present invention. FIG. 1 depicts a pressurized state when a wearer wears a mask or other devices providing the foregoing supply environment. The mask or other devices worn on the head or the face of the wearer could be regarded as an interface which provides guidance for an external continuous positive pressure respiratory device or other supply devices capable of providing breathable air to the wearer, so as to supply air or other breathable gases to the terminal of the wearer.

It could be understood from FIG. 1 that, when the interface is worn, a more sensitive facial region directly receives a pressure. The interface, for example, allows the mask or other devices to be fixed on the face or the head of the wearer by using a flexible elastic band or other units. A good interface is capable of automatically and appropriately distributing the pressure received on the facial region of the wearer in all wearing situations (e.g., the level of tightness of the elastic band adjusted by the same wearer each time when the mask or other devices are worn is not always the same, and so on), so that the wearer could be guided to a preferred wearing situation by the adaptive system on the basis of appropriate feedback of the adaptive system when the wearer wears the mask or other devices. Thus, the adaptive system can also further offer the face of the wearer with a preferred pressure distribution during wearing, further providing the wearer with comfort and ease. Since most wearers wearing the interface are patients, for example, patients suffering from obstructive sleep apnea (OSA) or patients suffering from other illness and needing to be supplied with breathable gases, the interface (or referred to as a patient interface) adapted with the adaptive system can bring the patients with more comfortable treating environments.

As shown in FIG. 1, the adaptive system includes a forehead pressure diffusing portion S1, a cheek buffering portion S2 and a connecting portion S3. When the user wears the interface, the pressure acting on the forehead pressure diffusing portion S1 and the pressure acting on the cheek buffering portion S2 could be transmitted by the connecting portion S3 serving as a transmission medium, thereby enabling the adaptive system to activate the self-adjusting capability. When the interface is worn, most of the pressure applied on the face of the wearer by the interface is depicted as a forehead pressure P1 and a cheek pressure P2 in FIG. 1 (only one side of the face is shown), wherein the area and the force of the pressure received by the cheek portion are in average greater than those of the forehead portion.

When the interface is worn, the forehead pressure diffusing portion S1 is pulled to lean close towards the surface of the forehead of the wearer, and the cheek buffering portion S2 of the interface is pulled to lean towards the surfaces of the cheeks of the wearer. On the basis of a leverage effect and the greater area and force of the pressure received by the cheek portions, the crushing of the cheek buffering portion S2 generated from the pressure received causes the connecting portion S3 to produce a pulling force PA2 upon the forehead pressure diffusing portion S1, wherein an action direction of the pulling force PA2 substantially causes the forehead pressure diffusing portion S1 to be away from the surface of the forehead of the wearer.

In the above situation, the configuration of the forehead pressure diffusing portion S1 is critical to the level of counteracting the pulling force PA2 and the level of influence on the cheek buffering portion S2. Apart from counteracting the pulling force PA2, when the forehead pressure diffusing portion S1 in the adaptive system is moved close to the forehead of the wearer as much as possible, a reverse leverage effect (opposite to the leverage effect in the foregoing paragraph) formed by the connecting portion S3 produces on the cheek buffering portion S2 a pulling force PA1 for alleviating the cheek pressure P2. With these two pulling forces PA1 and PA2 modulated in combination by the connecting portion S3 as well as the special configurations of the forehead pressure diffusing portion S1 and the cheek buffering portion S2, the adaptive system can generate appropriate feedback in response to the operation of the wearer, further enabling the interface to be guided to a better wearing condition by using the adaptive system.

Figure 2:
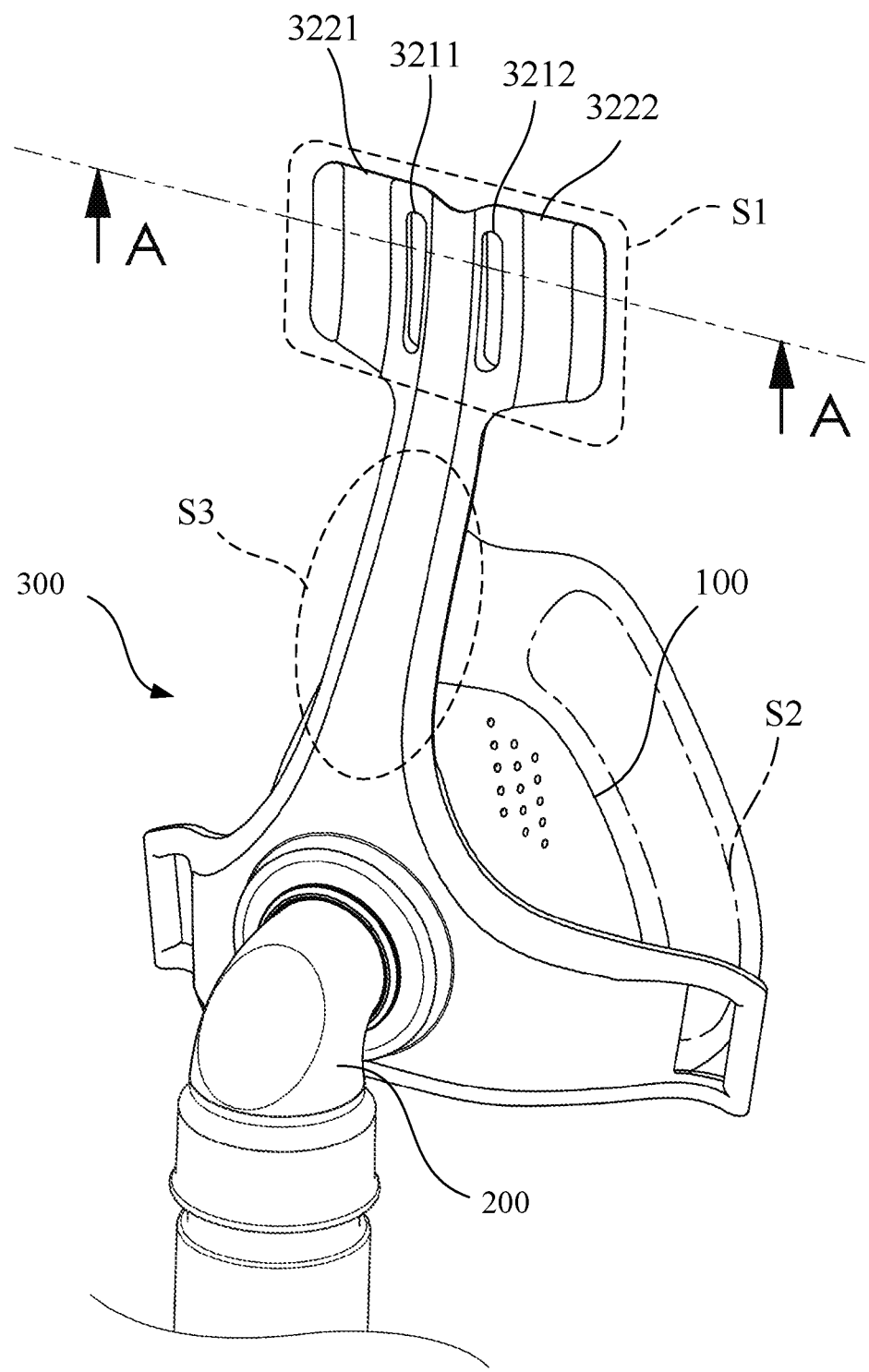
FIG. 2 is a perspective diagram of an adaptive system applied to a patient interface according to an embodiment of the present invention.
Figure 3:
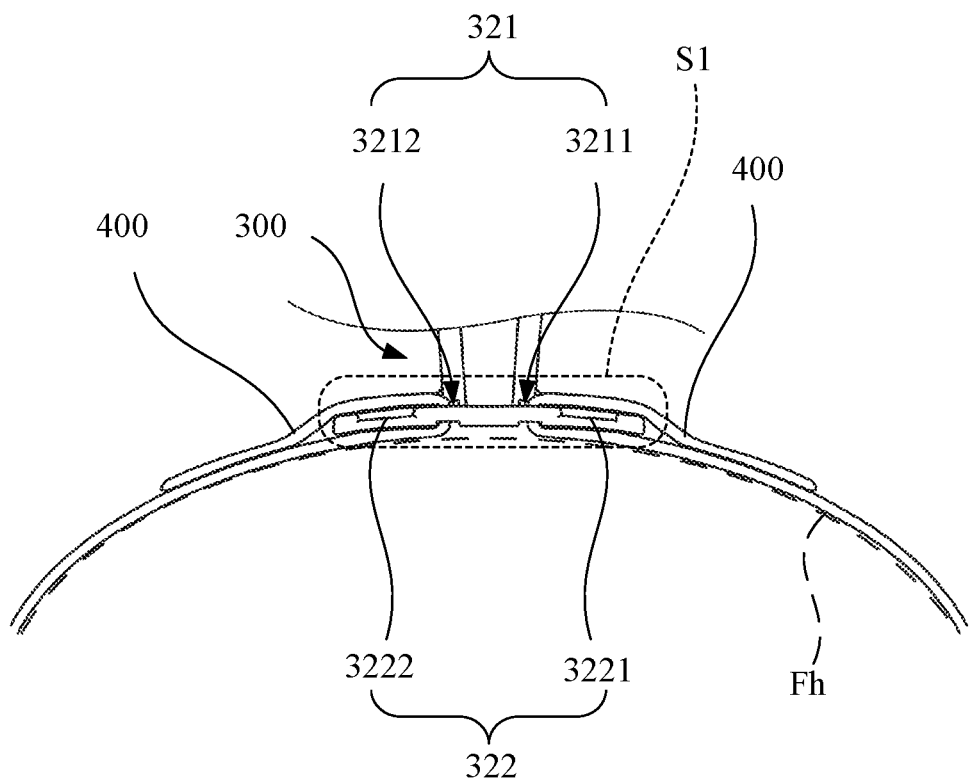
FIG. 3 is a partial enlarged schematic diagram of a connecting position of a forehead pressure diffusing portion and a headgear in FIG. 2.

Refer to FIG. 2 and FIG. 3. FIG. 2 shows a perspective diagram of an adaptive system applied to a patient interface according to an embodiment of the present invention. FIG. 3 shows a partial enlarged schematic diagram of a connecting position of the forehead pressure diffusing portion and the headgear in FIG. 2. The patient interface includes a cushion module 100, an elbow module 200, a frame module 300 and a headgear 400. The cushion module 100 and the elbow module 200 are connected to the frame module 300, air or other breathable gases are transported to the cushion module 100 through the elbow module 200, and the cushion module 100 may be a nasal mask or an oronasal mask supplied to the nose or the mouth and nose of the wearer. In the drawings of the present invention, the cushion module 100 is exemplified by an oronasal mask.

The forehead pressure diffusing portion S1 of the adaptive system is configured on one end of the frame module 300, and the headgear 400 could be connected on the frame module 300 through a headgear connecting portion 321 on the forehead pressure diffusing portion S1. Refer to FIG. 3 showing an example of the forehead pressure diffusing portion S1 tied with the headgear 400, under the pulling force of the headgear 400, a situation where the forehead pressure diffusing portion S1 is fitted close to the forehead surface Fh is shown. The headgear connecting portion 321 on the forehead pressure diffusing portion S1 is for connecting the headgear 400, and the forehead pressure diffusing portion S1 includes two side wings 322 deformable as the headgear 400 applies a pressure.

In FIG. 2 and FIG. 3, the headgear connecting portion 321 on the forehead pressure diffusing portion S1 is exemplified by a first headgear connecting portion 3211 and a second headgear connecting portion 3212 in a through-hole form. For example, the headgear 400 passing through the through hole of the headgear connecting portion 321 could be fixed by adhering back to the headgear 400 itself by self-adhesion of a hook-and-loop fastener, or fixed by other fixing means (e.g., clamping). In addition to being used for connecting the headgear 400, it is an important influence that the headgear connecting portion 321 makes use of the pulling force produced by the headgear 400 when the patient interface is worn to cause the deformation of the side wings 322 of the forehead pressure diffusing portion S1, such that the forehead pressure diffusing portion S1 is pulled close towards the forehead of the wearer as much as possible.

In the example in FIG. 2 and FIG. 3, the headgear 400 connected to the headgear connecting portion 321 serves as a contact interface between one end (the forehead pressure diffusing portion S1) of the frame module 300 and the forehead of the wearer; that is, the headgear 400 is directly in contact with the forehead surface Fh of the wearer. Thus, a larger contact area is provided between the patient interface and the forehead surface of the wearer (by the headgear 400 and the deformation of the side wings 322), thereby further producing a uniformized pressure diffusing effect for the pressure acting on the forehead surface of the wearer.

Figure 4:
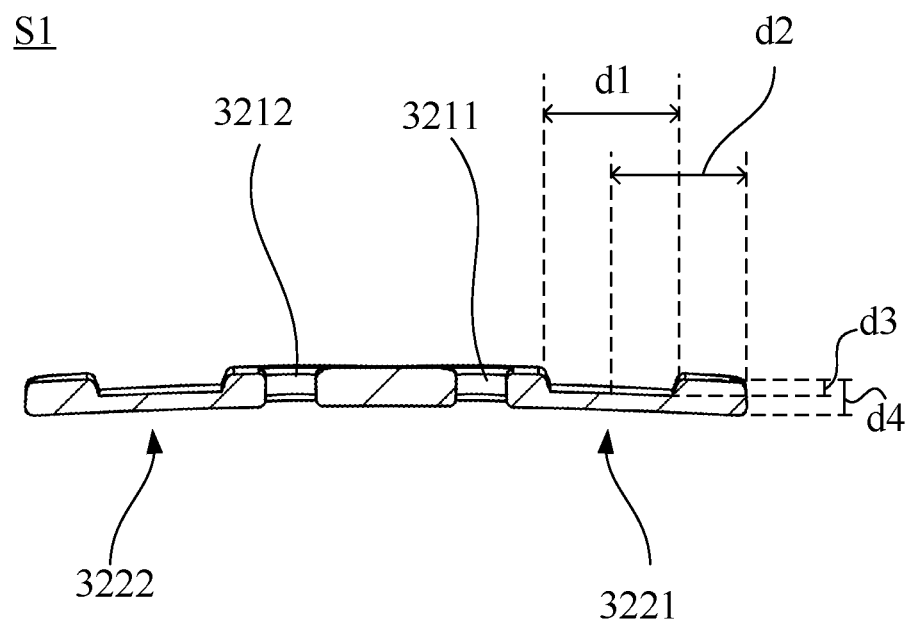
FIG. 4 is a sectional diagram of the forehead pressure diffusing portion along a section line AA in the embodiment in FIG. 2.

Refer to FIG. 2 to FIG. 4. FIG. 4 shows a sectional diagram of the forehead pressure diffusing portion along a section line AA in the embodiment in FIG. 2. In the examples in FIG. 2 to FIG. 4, a first side wing 3221 and a second side wing 3222 on the forehead pressure diffusing portion S1 provide a deformation capability by indentations on the side wings when the side wings receive an external force. One or a plurality of indentations could be present on the side wings, and the thickness of the side wings could be reduced by means of the indentations to further provide deformation when the side wings are pressed by the headgear. In the example in FIG. 2 and FIG. 3, each of the side wings is provided with one indentation having a width d1. For example, the width d1 of each indentation may be more than 1 mm. Furthermore, a distance d2 from a side edge of each side wing to a center line of the corresponding indentation may be at least 4 mm, preferably 7 mm to 9 mm. The extension length of the side wings gets larger as the value of d2 increases. In addition, an indentation depth d3 of each side wing is preferably not more than ⅔ of the thickness of each side wing; that is, the thickness of the indentation of each side wing is greater than ⅓ of a thickness d4 of the side wings.

Figure 5:
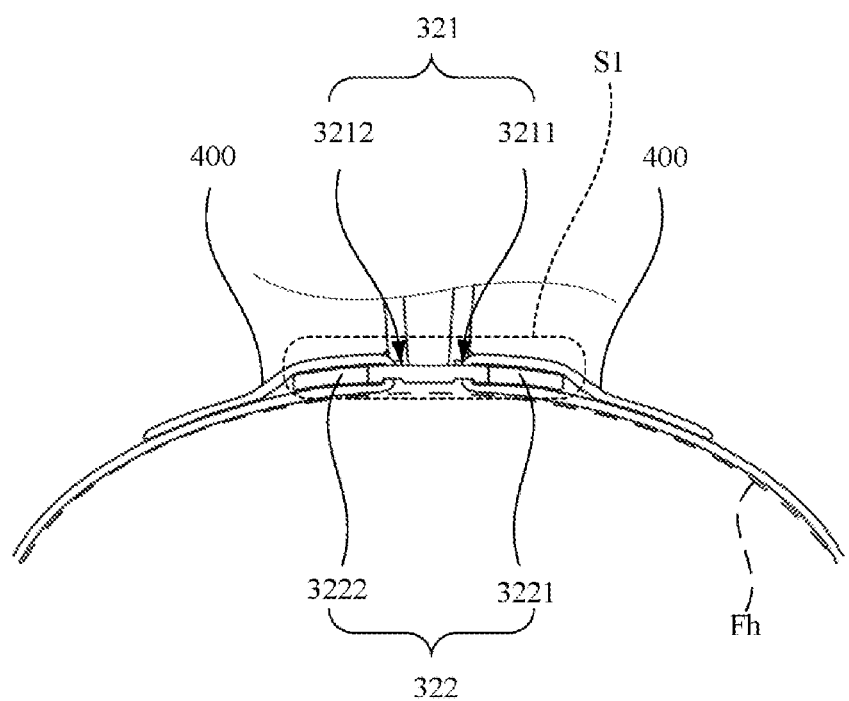
FIG. 5 is a partial enlarged schematic diagram of a connecting position of a forehead pressure diffusing portion and a headgear according to another embodiment of the present invention.

FIG. 5 shows a partial enlarged schematic diagram of a connecting position of a forehead pressure diffusing portion and a headgear according to another embodiment of the present invention. Compared to FIG. 3, the side wings 322 and the headgear connecting portion 321 shown in FIG. 5 are made of two different materials, wherein the elasticity of the side wings 322 is greater than the elasticity of the headgear connecting portion 321. For example, the material of the side wings 322 may be one selected from a thermoplastic material, a polymer material, a colloid and a foam material, while the material of the headgear connecting portion 321 may be one selected from a thermoplastic material, a polymer material, and a foam material. In the implementation form in FIG. 3, the side wings 322 and the headgear connecting portion 321 may be the same material, e.g., both using a thermoplastic material.

Again referring to FIG. 2, the cheek buffering portion S2 in the adaptive system is configured in the cushion module 100. The cheek buffering portion S2 in the cushion module 100 provides, by including at least two cushion wall thicknesses, a buffering force by the compression change of the cushion module 100 when the patient interface is worn. Accordingly, the headgear can produce the pulling force for triggering the deformation of the two side wings 322 when the patient interface is worn, enabling the forehead pressure diffusing portion S1 in the adaptive system to be pulled close towards the forehead of the wearer as much as possible to counteract the pulling force PA2 shown in FIG. 1 and also to alleviate the cheek pressure P2 caused by the cheek buffering portion S2 upon the face of the wearer. Furthermore, without using a forehead pad, the patient interface can modulate in combination the two pulling forces PA1 and PA2 to have the wearer experience a better wearing environment. Furthermore, because no forehead pad is involved, production costs of the patient interface are reduced, and it is more convenient for the wearer to maintain or clean a patient interface or a respiratory mask having the adaptive system of the embodiment of the present invention.

Figure 6:
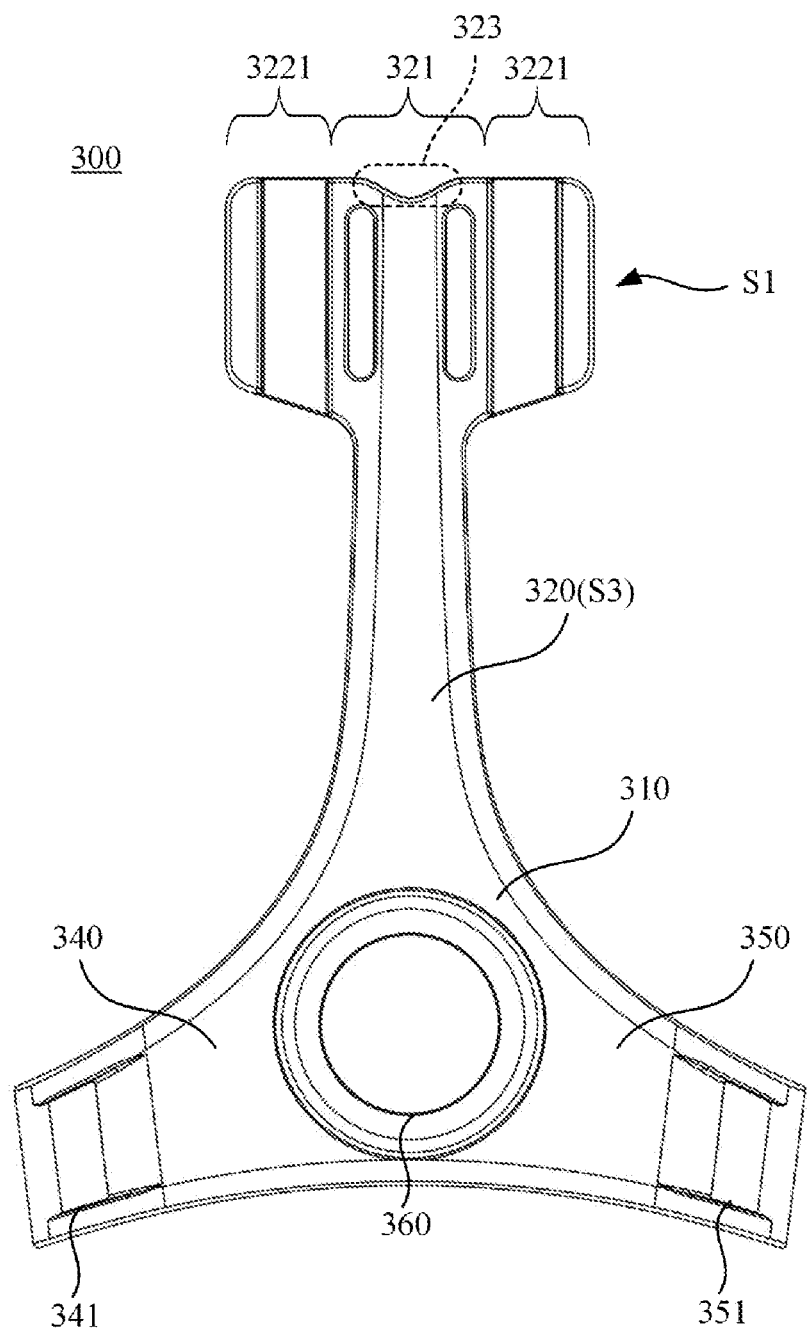
FIG. 6 is a perspective diagram of a frame module in the embodiment in FIG. 2.

FIG. 6 shows a perspective diagram of the frame module in the embodiment in FIG. 2. The frame module 300 includes a body 310, a connecting portion 320, and two lateral extension elements 340 and 350. The body 310 includes a coupling opening 360 for installing the elbow module 200. The connecting portion 320 (S3) extends from the top of the body 310, and an end portion of the connecting portion 320 (S3) is the forehead pressure diffusing portion S1, wherein the forehead pressure diffusing portion S1 includes the headgear connecting portion 321 and the two side wings 3221 and 3222 located on the two sides of the headgear connecting portion 321. The two lateral extension elements 340 and 350 extend from two sides of the body 310, and end portions of the two lateral extension elements 340 and 350 are provided with respective through holes 341 and 351 for the headgear to pass through. The expression "the through holes 341 and 351 for the headgear to pass through" include directly passing through or indirectly passing through. For example, the form of passing through shown in FIG. 1 is indirectly passing through, that is, the headgear first passes through an additional fastening ring 410, and the fastening ring 410 is fastened to the through holes on the frame module 300. Furthermore, a notch 323 could be provided at an extension end of the forehead pressure diffusing portion S1 at the connecting portion 320. The notch shape of the notch 323 may be a triangle or a trapezoid, so as to further reduce the contact area between the connecting portion 320 (S3) of the frame module 300 and the forehead of the wearer to further improve wearing comfort.

Figure 7:
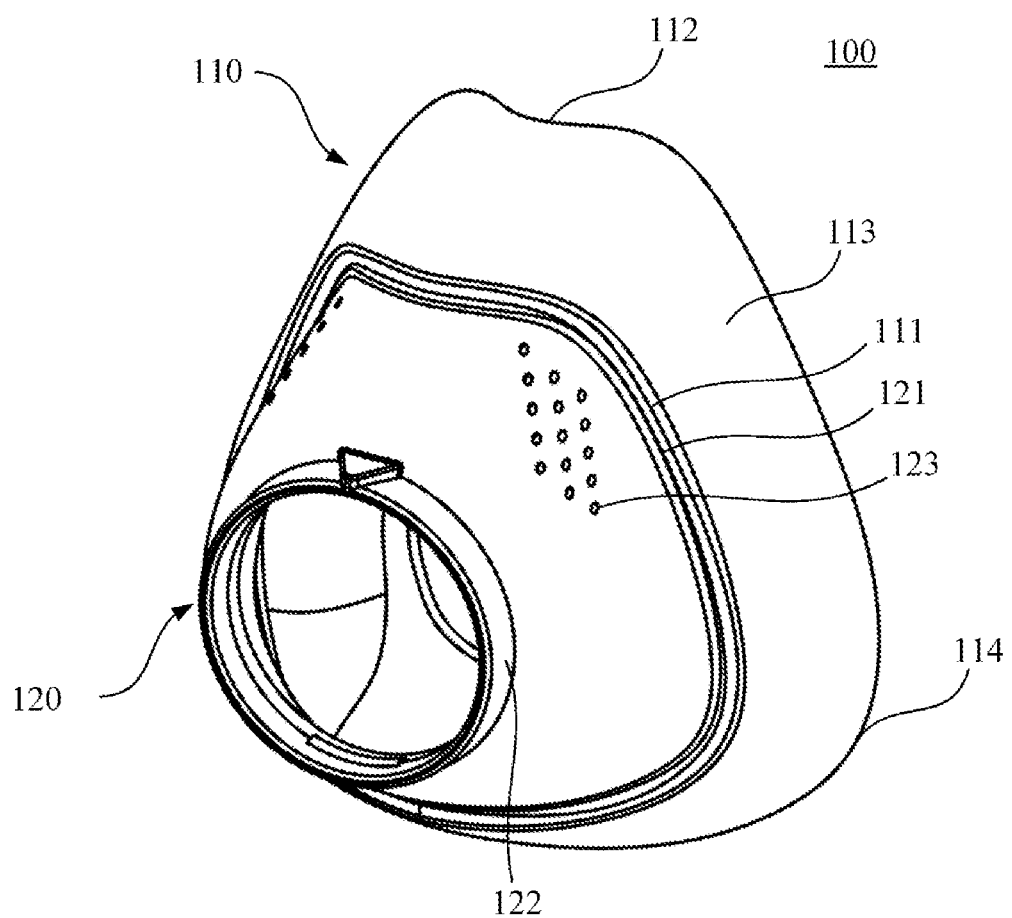
FIG. 7 is a perspective diagram of a cushion module in the embodiment in FIG. 2.

FIG. 7 shows a perspective diagram of the cushion module in the embodiment in FIG. 2. The cushion module 100 could be detachably assembled to an inner side of the body 310 of the frame module 300 (the elbow module 200 is assembled from an outer side of the body 310) by at least one assembly structure of the assembly region 122 in the front. The cushion module 100 includes a deformation portion 110 and a non-deformation portion 120. The deformation portion 110 plays a role of the cheek buffering portion S2 in the patient interface. The non-deformation portion 120 fixes the deformation portion 110, and also transmits by the connecting portion S3 of the frame module 300 a crushed state of the cheek buffering portion S2 generated due to a pressure received, so as to further produce a pulling force PA2 (see FIG. 1) upon the forehead pressure diffusing portion S1.

As shown in FIG. 7, the deformation portion 110 includes a first coupling region 111, a nose portion 112, a buffer region 113 (also refer to FIG. 8), and a face contacting region 114. The buffer region 113 extends downwards from the nose region 112. The non-deformation portion 120 includes a second coupling region 121 and an assembly region 122. The face contacting region 114 of the deformation portion 110 can include a wearing port covering only the nose of the wearer or a wearing port simultaneously covering the mouth and the nose of the wearer. Furthermore, the first coupling region 111 and the second coupling region 121 may be permanently coupled; for example, shaping and connection could be completed by using wrapped injection. Thus, by the adaption of the material and/or thickness of the cushion module of the buffer region 113, the buffer region 113 can serve as a buffer interface of the pressure between the frame module 300 and the face of the wearer, so as to enable the deformation portion 110 to be adaptively fitted to the face of the wearer when the frame module 300 is worn. The material of the deformation portion 110 of the cushion module 100 may be an elastic material, e.g., silicone.

In other embodiments, the elasticity of the buffer region 113 could be larger than the elasticities of the first coupling region 111, the nose region 112 and the face contacting region 114. The deformation portion 110 could achieve a configuration having different elasticities by the buffer region 113 having a thickness greater than those of cushion walls or a part of cushion walls of the first coupling region 111, the nose region 112 and the face contacting region 114.

In other embodiments, the non-deformation portion 120 may include at least one release opening region which may be configured near the nose region 112 of the deformation region 110. The release opening region has a plurality of vent holes 123. The vent holes 123 are configured at positions such that, when the patient interface is worn, the vent holes 123 are distributed above nose wings of the wearer (substantially as the exemplary positions shown in FIG. 7).

Figure 8:
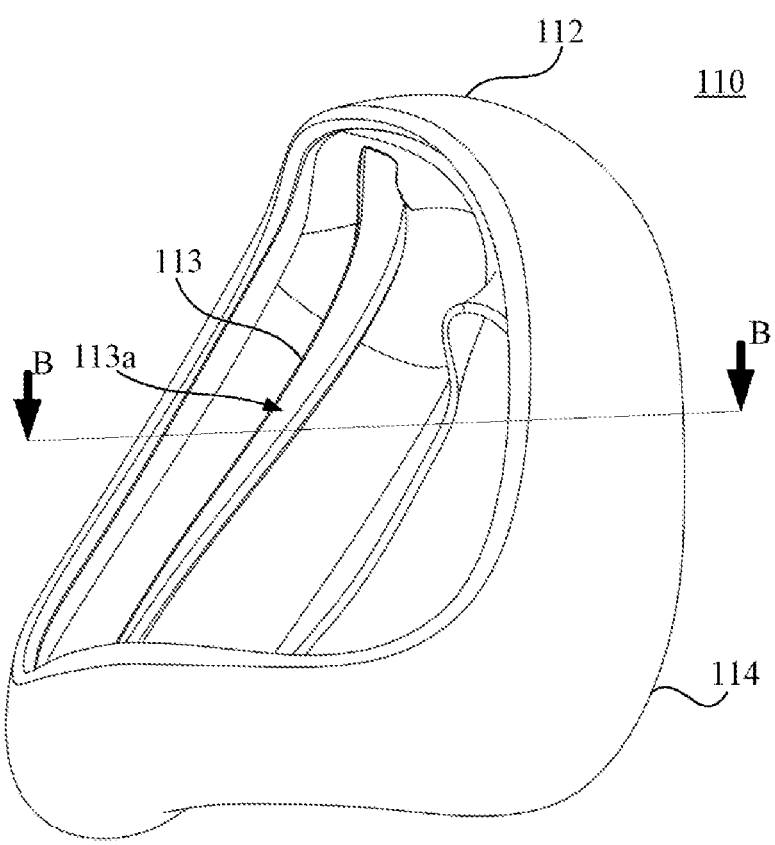
FIG. 8 is a perspective diagram of a deformation portion of the cushion module of the embodiment in FIG. 2 from another perspective angle.
Figure 9:
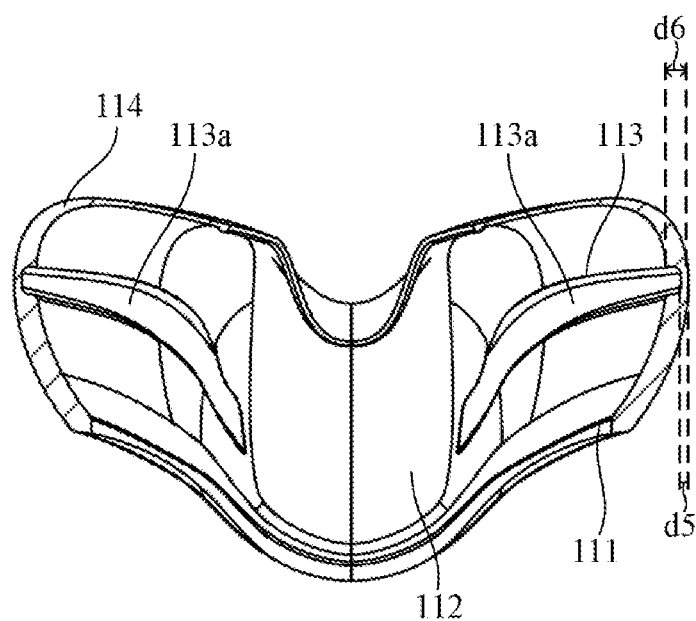
FIG. 9 is a sectional diagram of a deformation portion of the cushion module along a section line BB in the embodiment in FIG. 2.

Refer to FIG. 8 and FIG. 9. FIG. 8 shows a perspective diagram of the deformation portion of the cushion module in the embodiment in FIG. 2 from another perspective angle. FIG. 9 shows a sectional diagram of the deformation portion of the cushion module along a section line BB in the embodiment in FIG. 2. As shown in FIG. 8, the buffer region 113 of the deformation portion 110 achieves different changes in elasticity by changing the cushion wall thicknesses to further produce a buffer effect. The buffer region 113 is configured with a groove structure. More specifically, a groove 113a extending longitudinally is provided on each of two inner side edges of the deformation portion 110 (only one inner side is depicted in FIG. 8) corresponding to the cheeks. The width of the groove 113a appears tapered from the top to the bottom (wherein the top refers to the nose region 112) or conic (wherein the bottom of the cone refers to the nose region 112). The width ratio of a widest part to a narrowest part of the groove 113a may be approximately 6:1; for example, the width of the widest part may be approximately 12 mm and the width of the narrowest part may be approximately 2 mm; alternatively, the width of the widest part may be approximately 4 mm and the width of the narrowest part may be approximately 0.6 mm. The widths of the widest part and the narrowest part may be configured according to whether the cushion module is a nasal mask or an oronasal mask. The cushion wall thickness near the groove 113a (a non-groove position) usually drastically decreases from the groove towards a direction opposite to the first coupling region 111. Furthermore, in other embodiments, the cushion thickness of the groove 113a of the buffer region 113 could be smaller than the cushion thicknesses of the nose region 112 and the face contacting region 114. Further, in other embodiments, the cushion thickness of the groove 113a of the buffer region 113 could be smaller than a longitudinal extension depth of the groove 113a, so as to preserve a certain level of buffering capability of the cheek buffering portion S2. Furthermore, the longitudinal extension depth of the groove 113a extends from the top (close to the nose region 112) of the groove 113a towards the bottom of the face contacting region 114.

Figure 10:
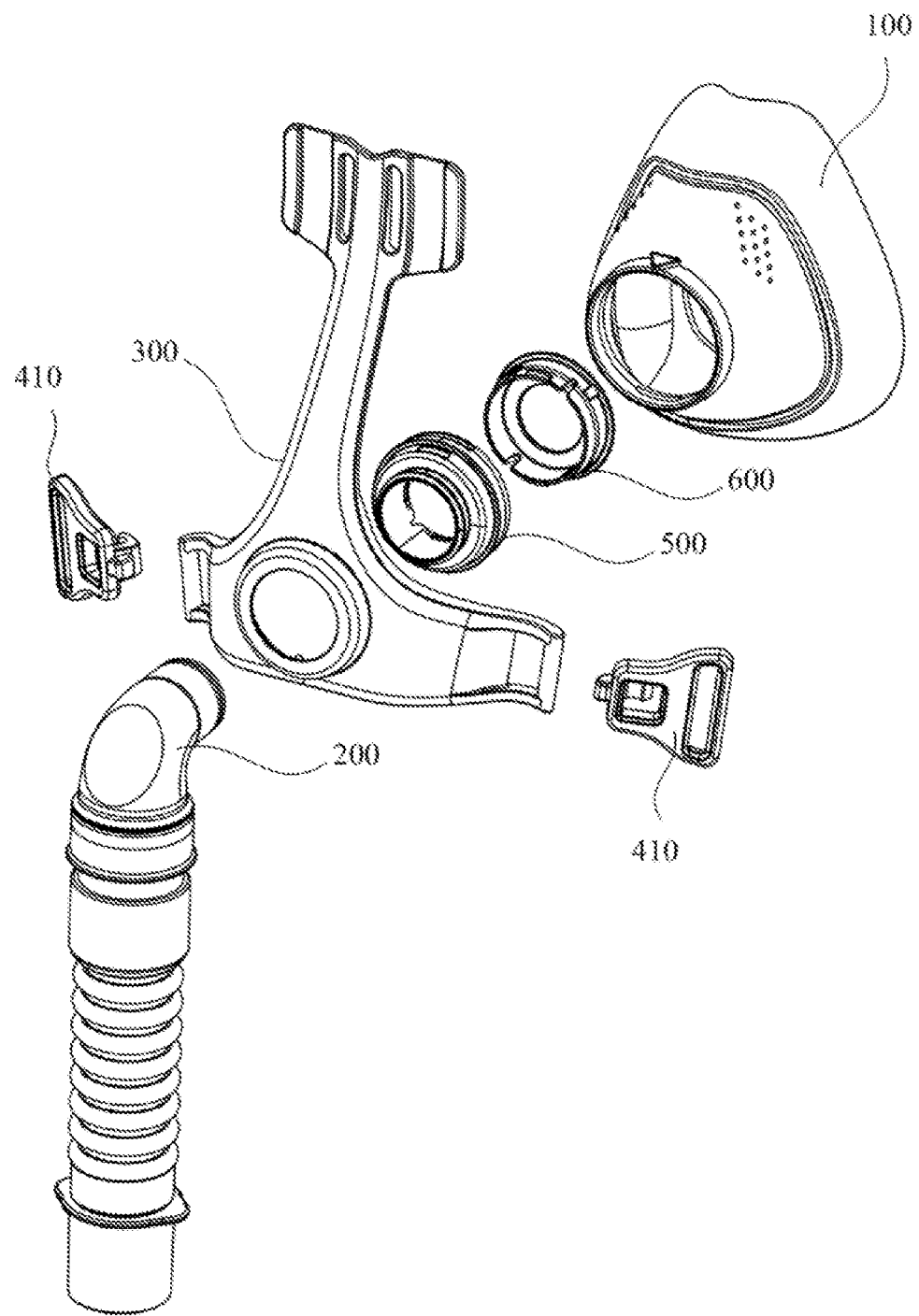
FIG. 10 is an exploded schematic diagram of a respiratory mask according to another embodiment of the present invention.
Figure 11:
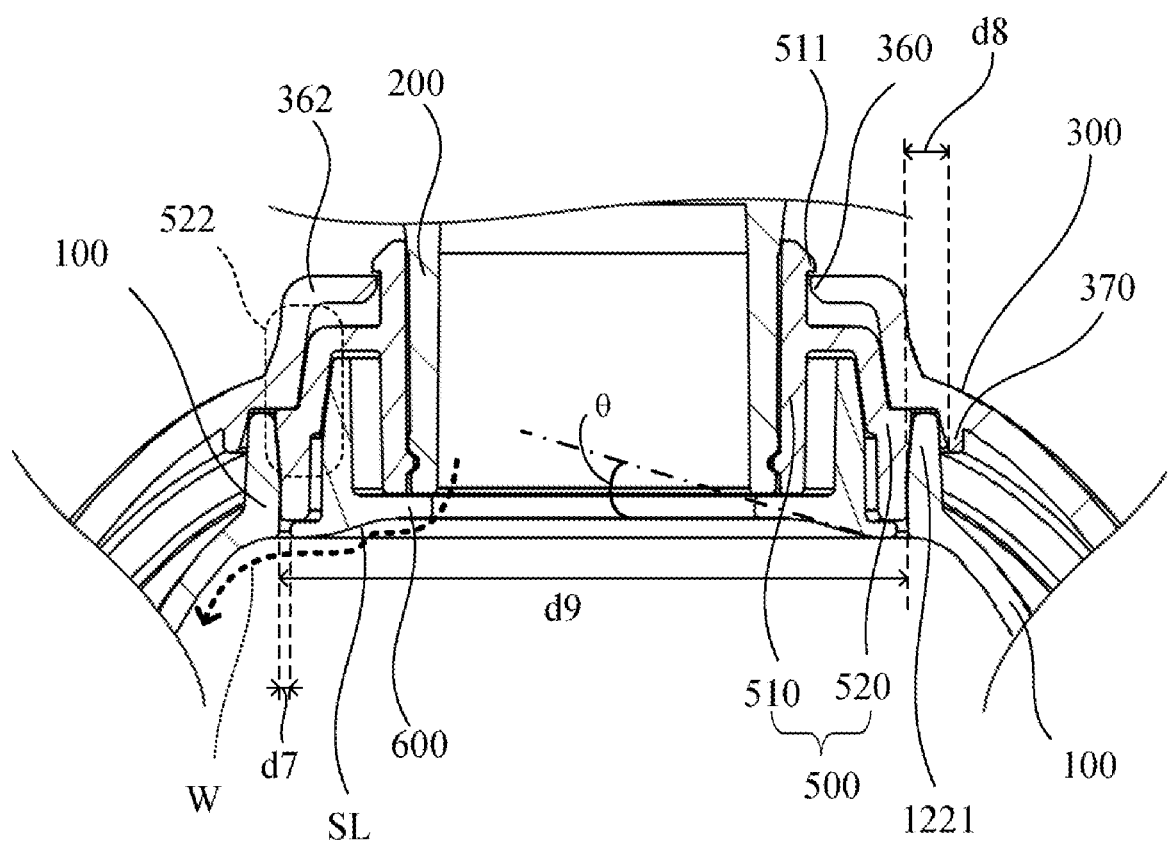
FIG. 11 is a partial sectional diagram of the respiratory mask in FIG. 10.

Refer to FIG. 10 and FIG. 11. FIG. 10 shows an exploded schematic diagram of a respiratory mask according to another embodiment of the present invention. FIG. 11 shows a partial sectional diagram of the respiratory mask in FIG. 10. The respiratory mask according to this embodiment includes a cushion module 100, an elbow module 200, a frame module 300, a headgear 400 (refer to FIG. 3 or FIG. 4), a connecting ring 500, a covering ring 600, and the foregoing adaptive system (configured in the frame module 300 and the cushion module 100). FIG. 10 shows an example of the frame module 300 connected to the headgear through two fastening rings 410 fastened thereto.

The connecting ring 500 includes an inner pipe portion 510, and an outer periphery portion 520 connected to the inner pipe portion 510 and encircling the inner pipe portion 510. The inner pipe portion 510 protrudes a part thereof from the body 310 towards a front surface of the frame module 300 after the inner pipe portion 510 is installed to the coupling opening 360 of the frame module 300. The protruding part of the inner pipe portion 510 is provided with a fastening edge 511 at an end edge thereof, and the connecting ring 500 could be fastened on the coupling opening 360 by the fastening edge 511, so as to fix the connecting ring 500 on the frame module 300. Furthermore, an end portion of the inner pipe portion 510 of the connecting ring 500 protruding from the front surface of the frame module 300 includes the fastening edge 511, an extension flange 362 encircling the coupling opening is provided on the front surface of the frame module 300, and the fastening edge 511 is for fastening with the extension flange 362. The outer periphery portion 520 of the connecting ring 500 is provided with a step structure 522 which is for abutting near a flange 370 of the frame module 300. An inner side of the extension flange 362 of the frame module 300 could be additionally configured with a positioning rod, and the outer periphery portion 520 of the connecting ring 500 could be provided with a positioning hole for the positioning rod to pass through, so as to more securely install the connecting ring 500 on the frame module 300.

The inner pipe portion 510 may be detachably combined with the elbow module 200. The outer periphery portion 520 matches with the frame module 300 (the part is the body of the frame module) so as to detachably combine with the cushion module 100 (the part is the non-deformation portion of the cushion module). The outer periphery portion 520 and the flange 370 on the frame module 300 form an assembly gap d8 for receiving the front air transporting opening (the assembly region 122 shown in the embodiment in FIG. 7) of the cushion module 100, wherein the assembly gap d8 gradually expands towards the direction of a rear surface of the frame module 300.

A periphery of the front air transporting opening of the cushion module 100 is provided with an assembly collar 1221. An inner diameter d9 of the assembly collar 1221 gradually shrinks towards the direction of the rear surface of the frame module 300. With the aid of the flange 370 on the frame module 300, abutment could be formed between an inner surface of the assembly collar 1221 of the cushion module 100 and an outer surface of the outer periphery portion 520 of the connecting ring 500, thereby further enhancing airtightness.

The elbow module 200 includes therein an air duct, and the elbow module 200 is detachably assembled to the frame module 300 through the connecting ring 500. The body 310 of the frame module 300 is provided with a coupling opening 360. The cushion module 100 is also detachably assembled to the frame module 300 through the connecting ring 500. The covering ring 600 covers the connecting ring 500 and reveals the air duct, and could mask the structure of the connecting ring 500. Furthermore, the covering ring 600 has an inclined surface SL which extends in an oblique manner in a direction from an inner periphery of the covering ring 600 towards an inner periphery of the cushion module 100 to present the inclined surface SL. The inclined surface SL is for guiding moisture or other fluids to flow downwards along the inclined surface SL of the covering ring 600 and an inner arc surface of the cushion module 100 (as shown by a flowing path W), and to cause water to gather at a folded portion on the inner side of the cushion module 100, such that the fluids do not directly drip down from near the air duct of the elbow module 200. Since the wearer generally lies down when the respiratory mask is worn, the air duct of the elbow module in the mask may easily be higher than the mouth and the nose of the wearer. Thus, by further guiding the fluids, the wearer is prevented from a situation of being dripped by the fluids, hence further improving comfort of the wearer. Such fluid guiding effect is more essential with respect to a wearer using a humidifier.

As shown in FIG. 11, an obliquely extending outer periphery of the covering ring 600 is spaced from the cushion module 100 by a flow guide gap d7 of 0.1 mm to 5 mm. The covering ring 600 includes an inclined portion and a planar portion. The inclined portion has the inclined surface SL and encircles the outer side of the planar portion, and an included angle θ between the inclined surface and a horizontal reference plane of the planar portion is between 0 degree and 90 degrees.

Figure 12:
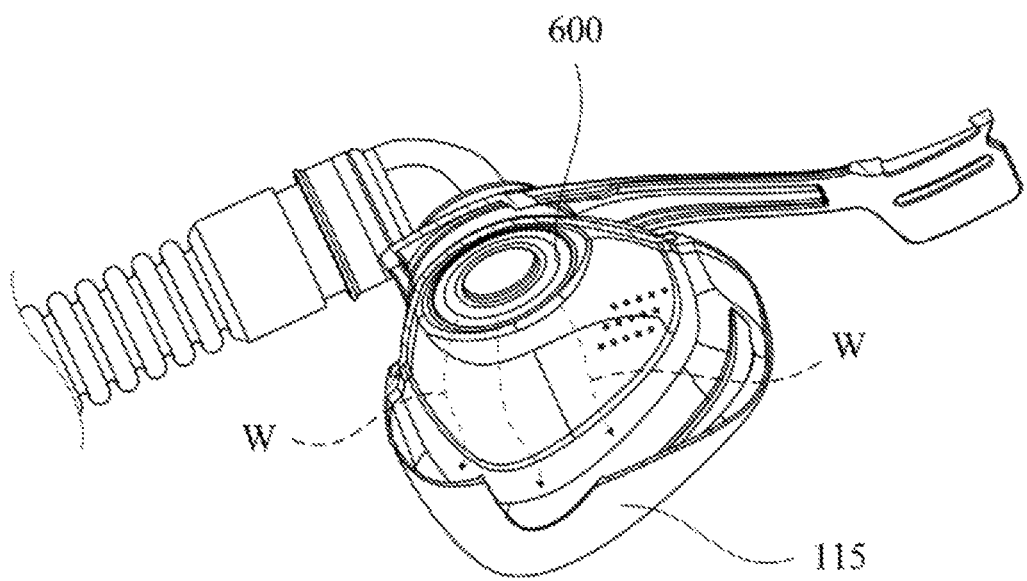
FIG. 12 is a sectional diagram of the respiratory mask in FIG. 10 from another perspective angle.

Refer to FIG. 12 showing a sectional diagram of the respiratory mask in FIG. 10 from another perspective angle. FIG. 12 further illustrates the function of the covering ring 600. With the inclined surface SL, a fluid gradually adhered to an inner edge and hence accumulated in the respiratory mask can flow downwards along the arc surface in the mask, and the fluid can gather at a folded portion 115 on the inner side of the cushion module 100. Furthermore, the material of the covering ring 600 may be selected from a hydrophobic material so that further facilitate the guided flow of fluids.

In conclusion, with the configuration of the adaptive system, as the level of tightness is adaptively adjusted by a wearer during wearing, forces received upon the face of the wearer could be automatically and appropriately distributed to improve comfort of the wearer. When the cushion module, the elbow module, and the headgear are assembled, the adaptive system is adapted to fit the contours of wearer's face. Further, with the matching structures of the components on the mask structure, the overall structure of the mask is kept firm, and the special configuration of the covering ring can further avoid the drawback of fluids dripping onto the face of the wearer, thereby significantly improving comfort of the wearer.

The present disclosure is illustrated by various aspects and embodiments. However, persons skilled in the art understand that the various aspects and embodiments are illustrative rather than restrictive of the scope of the present disclosure. After perusing this specification, persons skilled in the art may come up with other aspects and embodiments without departing from the scope of the present disclosure. All equivalent variations and replacements of the aspects and the embodiments must fall within the scope of the present disclosure. Therefore, the scope of the protection of rights of the present disclosure shall be defined by the appended claims.

What is claimed is:

1. A patient interface, comprising:
   a cushion module;
   an elbow module;
   a frame module positioned between the cushion module and the elbow module;
   a headgear removably attached to the frame module; and
   an adaptive system, adapted to fit the contours of patient's face when the cushion module, the elbow module, and the headgear are assembled, the adaptive system comprising:
      a forehead pressure diffusing portion disposed in the frame module;
      a cheek buffering portion disposed in the cushion module; and
      a connecting portion positioned between the forehead pressure diffusing portion and the cheek buffering portion, wherein the connecting portion is configured to transmit pressure between the forehead pressure diffusing portion and the cheek buffering portion,
      wherein the forehead pressure diffusing portion comprises:
         two side wings; and
         a headgear connecting portion adapted to connect the headgear, and located between the side wings,
   wherein the cushion module for assembling to the frame module comprises
      a deformation portion, comprising a first coupling region, a nose region, a buffer region and a face contacting region, wherein the buffer region extends downwards from the nose region,
      wherein the buffer region comprises a longitudinally extended groove on each of inner side edges of the deformation portion, wherein in the deformation portion, an elasticity of the buffer region is greater than those of the first coupling region, the nose region and the face contacting region.

2. The patient interface according to claim 1, wherein the two side wings are deformable by a pressure applied on the headgear.

3. The patient interface according to claim 2, wherein the headgear connected to the headgear connecting portion serves as a contact interface between the frame module and the forehead of the patient.

4. The patient interface according to claim 2, wherein each of the side wings comprises an indentation for providing deformation, the thickness of the side wings is thinner than the thickness of the headgear connecting portion, so as to provide deformation when the side wings are pressed by the headgear.

5. The patient interface according to claim 4, wherein a width of the indentation on each of the side wings is at least 1 mm.

6. The patient interface according to claim 4, wherein each of the side wings is configured to laterally extend at an end portion of the frame module, and a side edge of each of the side wings is distanced from a center line of the corresponding indentation by at least 4 mm.

7. The patient interface according to claim 2, wherein the side wings are made of a material different from that of the headgear connecting portion, and an elasticity of the side wings is greater than that of the headgear connecting portion.

8. The patient interface according to claim 1, wherein the cushion module for assembling to the frame module comprises:
   a non-deformation portion, comprising an assembly region and a second coupling region, wherein the assembly region is for detachably assembling to the frame module, and the second coupling region is permanently coupled with the first coupling region.

9. The cushion module according to claim 8, wherein in the deformation portion, an elasticity of the buffer region is greater than those of the first coupling region, the nose region and the face contacting region.

10. The cushion module according to claim 8, wherein the deformation portion and the non-deformation portion are shaped and coupled by wrapped injection.

11. The cushion module according to claim 8, wherein the non-deformation portion comprises at least one release opening region, the release opening region is configured near the nose region of the deformation region and has a plurality of vent holes, and the vent holes are distributed near above two nose wings of a patient when the frame module is worn.

12. The cushion module according to claim 8, wherein a width of each of the grooves appears tapered from top to bottom or conic.

13. The cushion module according to claim 8, wherein in the deformation portion, a cushion thickness of the grooves of the buffer region is smaller than cushion thicknesses of the nose region and the face contacting region.

14. The cushion module according to claim 8, wherein a cushion thickness of the grooves of the buffer region is smaller than a longitudinal extended depth of the grooves.

15. The cushion module according to claim 8, wherein in the non-deformation portion, the assembly region comprises at least one assembly structure.

16. The cushion module according to claim 8, wherein the face contacting region of the deformation portion comprises a wearing port covering only the nose of a patient or simultaneously covering the mouth and nose of the patient.

17. The cushion module according to claim 8, wherein the buffer region serves as a buffer interface for the pressure applied between the frame module and the face of a patient by using an appropriate configuration of a cushion material or thickness of the buffer region, such that the deformation portion is adaptively fitted to the face of the patient when the frame module is worn.

18. The patient interface according to claim 1, wherein a forehead pad is absent between the forehead pressure diffusing portion and the patient's forehead.

19. The patient interface according to claim 1, wherein the frame module comprises:
   a body, for assembling the elbow module and the cushion module;
   the connecting portion, extending from the body, an end portion of the connecting portion being the forehead pressure diffusing portion; and
   two lateral extension elements, respectively extending from two sides of the body, an end portion of each of the lateral extension elements having a through hole for the headgear to pass through.

20. The patient interface according to claim 1, wherein the forehead pressure diffusing portion further comprises:
   a connecting ring, configured at a coupling opening on a body of the frame module, the connecting ring being for the elbow module and the cushion module to be detachably assembled to the frame module; and
   a covering ring, covering the connecting ring and revealing an air duct of the elbow module, the covering ring having an inclined surface on a surface opposite to the frame module.

21. A respiratory mask, comprising:
   a cushion module;
   an elbow module, having an air duct;
   a frame module positioned between the cushion module and the elbow module;
   a headgear removably attached to the frame module;
   a connecting ring, configured at a coupling opening on a body of the frame module, the connecting ring being for the elbow module and the cushion module to be detachably assembled to the frame module;
   a covering ring, covering the connecting ring and revealing the air duct, the covering ring having an inclined surface on a surface opposite to the frame module; and
   an adaptive system, adapted to fit the contours of patient's face when the cushion module, the elbow module, and the headgear are assembled, the adaptive system comprising:
      a forehead pressure diffusing portion disposed in the frame module;
      a cheek buffering portion disposed in the cushion module; and
      a connecting portion positioned between the forehead pressure diffusing portion and the cheek buffering portion, wherein the connecting portion is configured to transmit pressure between the forehead pressure diffusing portion and the cheek buffering portion,
      wherein the forehead pressure diffusing portion comprises:
         two side wings; and
         a headgear connecting portion adapted to connect the headgear, and located between the side wings,
         wherein the rigidity of each of the side wings is lower than the rigidity of the headgear connecting portions.

22. The respiratory mask according to claim 21, wherein the connecting ring comprises:
   an inner pipe portion; and
   an outer periphery portion, connected to the inner pipe portion and encircling the inner pipe portion;
   wherein the elbow module is detachably assembled to the inner pipe portion, the outer periphery portion and a flange on the body of the frame module form an assembly gap for receiving a front air transporting opening of the cushion module, and the cushion module is detachably assembled to the body of the frame module through the assembly gap.

23. The respiratory mask according to claim 22, wherein a periphery of the front air transporting opening of the cushion module is provided with an assembly collar, an inner diameter of the assembly collar gradually shrinks backwards, and the flange on the body of the frame module is matchingly used to form abutment between an inner surface of the assembly collar of the cushion module and an outer surface of the outer periphery portion of the connecting ring to enhance airtightness.

24. The respiratory mask according to claim 22, wherein the inner pipe portion of the connecting ring comprises a fastening edge at an end portion protruding from a front surface of the frame module, the front surface of the body is provided with an extension flange encircling the coupling opening, the fastening edge is for fastening to the extension flange, the outer periphery portion of the connecting ring is provided with a step structure, and the step structure is for abutting near the flange of the body.

25. The respiratory mask according to claim 24, wherein an inner side of the extension flange of the body comprises a positioning rod, and the outer periphery portion of the connecting ring has a positioning hole for the positioning rod to pass through.

26. The respiratory mask according to claim 21, wherein the covering ring comprises an inclined portion and a planar portion, the inclined portion has the inclined surface and encircles an outer side of the planar portion, and an included angle between the inclined surface and a horizontal reference plane of the planar portion is between 0 degree and 90 degrees.

27. The respiratory mask according to claim 26, wherein an outer edge of the covering ring and the cushion module are distanced by a flow guide gap of 0.1 mm to 5 mm.

28. The respiratory mask according to claim 21, wherein the inclined surface of the covering ring enables water in the respiratory mask to flow downwards along the inclined surface of the covering ring and an inner arc surface of the cushion module, and to gather at a folded portion on an inner side of the cushion module.

29. The respiratory mask according to claim 21, wherein a material of the covering ring is a hydrophobic material.

\* \* \* \* \*